(12) United States Patent
Mayer

(10) Patent No.: US 6,221,083 B1
(45) Date of Patent: Apr. 24, 2001

(54) SYNCHRONIZED STAPLER/NEEDLE DRIVER/FORCEPS FOR MOTION IN ALL PLANES

(76) Inventor: Paul W. Mayer, 6290 SW. 92nd St., Miami, FL (US) 33156-1866

( * ) Notice: Subject to any disclaimer, the term of this patent is extended or adjusted under 35 U.S.C. 154(b) by 0 days.

(21) Appl. No.: 09/429,565

(22) Filed: Oct. 28, 1999

Related U.S. Application Data

(60) Provisional application No. 60/108,642, filed on Nov. 16, 1998.

(51) Int. Cl.$^7$ .................................................. A61B 17/10
(52) U.S. Cl. ............................................................. 606/139
(58) Field of Search .................................... 606/139, 144, 606/148, 147, 219, 205, 1, 206, 210; 600/569, 570, 572, 104, 109, 112, 127, 129, 587, 595

(56) References Cited

U.S. PATENT DOCUMENTS

| | | |
|---|---|---|
| 4,266,548 | 5/1981 | Davi . |
| 4,473,077 | * 9/1984 | Noiles et al. .......................... 606/219 |
| 4,671,445 | * 6/1987 | Barker et al. .......................... 606/219 |
| 5,618,294 | * 4/1997 | Aust et al. ............................. 606/205 |
| 5,752,973 | * 5/1998 | Kieturakis ............................. 606/205 |
| 5,766,187 | 6/1998 | Sugarbaker . |
| 5,817,111 | 10/1998 | Riza . |
| 5,827,291 | 10/1998 | Fucci et al. . |
| 5,830,220 | 11/1998 | Wan et al. . |
| 5,897,563 | 4/1999 | Yoon et al. . |

* cited by examiner

Primary Examiner—Henry J. Recla
Assistant Examiner—(Jackie)Tan-Uyen T. Ho
(74) Attorney, Agent, or Firm—Browdy and Neimark

(57) ABSTRACT

A suture needle holder (or stapler), especially for a heart operation such as anastomosis, has a free-floating armature (10) with a tip (11) having a rough anti-skid surface. Friction force between the tip and the surface of the heart drives the armature and keeps the tip at the site where it rests relative to the moving heart surface. The friction force, plus the force of a weak spring (103) pushing the armature forward, overcome the weight and inertia of the armature so that it remains at the operation site. The armature is slidably coupled to a handle barrel (100) through a bearing guide (110) but a slot (115) and pin (15) prevent axial rotations; the arm is unrestrained in the angle it makes with the axis of the barrel, but the arm cannot rotate about the barrel axis. Jaws (13, 31) at the tip of the arm may be used to grip a suture needle and the needle can be manipulated by rolling the barrel 100 so that the tip 11 rolls over the surface of the heart. One of the jaw (31) is actuated through a flexible cable (33) which does not affect the orientation or extension of the armature.

20 Claims, 3 Drawing Sheets

SYNCHRONIZED STAPLER/NEEDLE DRIVER/FORCEPS FOR MOTION IN ALL PLANES

CROSS REFERENCE TO RELATED APPLICATION

This application claims the benefit of provisional application Ser. No. 60/108,642, filed Nov. 16, 1998, entitled "Synchronized Stapler/Needle Driver/Forceps For Motion in All Planes", the contents of which are entirely incorporated herein by reference.

FIELD OF THE INVENTION

The present invention relates to surgical instruments, especially instruments with suturing or stapling tools.

REVIEW OF THE RELATED TECHNOLOGY

Surgical operations on most of the body's organs are uncomplicated by motion of that organ, but heart surgery is an exception. Heart operations are made much more difficult and dangerous by the heart's incessant beating.

The present inventor's U.S. Pat. No. 5,871,017, which is entirely incorporated herein by reference, shows a moving platform for supporting the arm of a surgeon who is operating on the heart. The platform moves in synchrony and isometrically with the motion of a point on the surface of the heart, carrying the surgeon's arm and operating hand with it and "stopping" the heart by eliminating the relative heart-hand motion. The heart is triggered by a pacemaker to keep its beating regular (this provides synchrony), and the platform driving mechanism is adjusted so that the platform and the surgeon's hand stay the same distance from the operation site on the heart during (providing isometry).

By virtually stopping the heart, the platform allows precise operation by the surgeon just as if both the hand and heart were still. This avoids the great expense and danger of actually stopping the heart with a heart-lung machine. In addition, the platform can be used with small "keyhole" chest openings; the heart does not need to be entirely exposed and the rib cage need not be opened.

The commercially-available Heartport system uses a small chest opening, but it requires stopping the heart and the use of a heart-lung machine. The *Wall Street Journal* of May 5, 1999, reported that the Heartport system has not lived up to expectations and is being abandoned by many cardiac surgeons trained in its use.

While the present inventor's moving platform is a significant advance, it has the minor drawbacks that the heart must be triggered for synchrony and that isometry can only be achieved by careful adjustment of both the platform hinge angle (base) to line up the motion vector and the platform driver mechanism (e.g., by selecting the proper one of various driving cams) to achieve synchrony and isometry. It is large and bulky, with numerous parts.

A variation on the theme of the moving platform is another invention of the present inventor, the motorized motion-canceling needle holder, disclosed in U.S. patent application Ser. No. 09/132,409, filed Aug. 11, 1998, the contents of which are entirely incorporated herein by reference. The motorized motion-canceling needle holder is a hand-held device about the size and shape of a small flashlight, with a protruding arm at one end. The arm tip is provided with suture needle-holding jaws, a stapler, or some other surgical tool. The arm automatically oscillates relative to the barrel or handle, driven via a flexible cable coupled to a drive mechanism. While the surgeon's hand holds the flash-light shaped handle stationary relative to the patient's chest, the drive mechanism causes the protruding tip of the arm to oscillate in synchrony and isometry with the motion of the heart; again the heart's motion is virtually, but not actually, stopped. The path of the tip can be made to follow any path by suitable curving the oscillating arm, which slides through guide holes; if the arm is curved near the guide hole, the tip will follow a non-linear path which matches the path of the site on the heart surface to be operated on. The motorized motion-canceling needle holder has no provision for changing the path of the tip while the device is oscillating.

The drive mechanism which oscillates the tip is generally similar to that which drives the moving platform (although the drive is indirect, through a cable). As with the moving platform, the heart is triggered by a pacer coupled to the drive mechanism. Unlike the platform, the orientation and positioning of the oscillation vector is not fixed, but is controlled by the hand of the surgeon holding the handle. The surgeon manipulates the handle to determine the angle and position at will. The surgeon activates the needle-clutching jaws or stapler device at the tip of the moving arm via a remote control, e.g., a foot switch.

As noted in the copending application on the motion-canceling needle holder, one limitation of the moving platform is that only the anterior surface of the heart is readily operated on because the lateral surfaces are buried deeply in the chest and when the platform is angled over far enough to align the platform motion vector with the heart surface motion vector, the other organs are in between the heart and the platform. The hand-held motion-canceling needle holder can be used in, for example, a quadruple bypass operation, where the platform cannot.

Despite the many advantages of the moving platform and the motion-canceling holder, these inventions are not as simple as is possible and therefore they are more costly than is optimum (although their cost is much less than that of many medical devices). In some cases, such as for patients in third-world countries, the reduced cost of the present invention might make the difference in saving a life.

Another disadvantage of the previous devices is that they are dependent on outside power (e.g. line current), which can fail or be interrupted while reserve generators are being activated.

Perhaps the greatest drawback of the previous devices is the need for careful adjustment in order to exactly follow the motion of the operation site on the heart. A new operation, or any change from one site to another during a single operation, may require a long and time-consuming adjustment. In the case of the moving platform, the base on which the platform is pivoted will need to be set up, the drive cam changed, the oscillation amplitude adjusted, and the pacer phase tweaked; for the motorized motion-canceling needle holder, a new arm having a different curvature may need to be substituted, and the same adjustments made to the drive mechanism as with the moving platform.

Besides the work of adjusting, the degree of adjustment possible with the previous inventions is limited. It may not be possible to completely eliminate all relative motion. The complexity of motion of the heart surface, any point of which does not move in a straight line or exhibit uniform acceleration, can be difficult to match, so that the platform or arm tip is not driven to follow the heart's motion exactly with absolute precision. Even with a selection of drive cams and bent arms, a perfect match to the actual motion cannot be achieved; there will always be some small decrement of the motion which must be compensated by the surgeon, making the operation more difficult and risky.

The prior art does not disclose an instrument for working on the surface of a moving organ such as the heart which is completely simple, reliable, inexpensive, and compact; which requires no outside power; and which requires no adjustment.

SUMMARY OF THE INVENTION

The invention thus provides such an instrument by using the heart (or other organ) surface to drive the instrument. A light-weight armature (arm), preferably made of hollow stainless steel tubing, "floats" within a hollow barrel in an arrangement which permits the tip of the armature (the operating portion) to move in any direction relative to the barrel. The forward end of the barrel, which is preferably tubular, is open; at the rear end is a plug, preferably of slippery plastic such as DELRIN, with a central guide hole through which the armature can slide, and which acts as a pivot point. Pivoting of the armature about the fulcrum of the guide hole is limited by the forward rim of the barrel.

A portion of the armature is encircled by a long coil spring. One end of the spring is fixed to the armature at a point back from the tip, the other end of the spring rests against (or is fastened to) the plug. Thus, when the tip of the armature is pressed backward the armature slides rearward through the hole in the plug, the spring is compressed, and the tip will follow the motion of whatever is pressing it backwards. (The armature is so light that the force of the spring keeps it in contact with the pressing surface.)

Thus the armature will follow forward-backward motion parallel to the barrel axis (because of the spring) and it also will follow side-to-side motion (because of the guide hole).

While the tip of the armature is free to move in all planes, the present invention includes means for preventing any relative rotation between the barrel and the armature along the axis parallel to the barrel extension or axis; holding the barrel in one hand and the armature in the other, no twisting is possible. While the tip of the armature is free to translate in any direction whatever, it will not spin or roll unless the barrel is rotated about its axis.

The tip is preferably roughened and rounded, and when rested against the surface of the moving heart with the coil spring slightly compressed, the tip will follow the motion of the heart. Since the tip is free to move in any plane, the barrel can be tilted and moved about without causing the tip of the armature to skid away from the site it rests on. The tip follows the heart's motion exactly and precisely, without any need for adjustments. There is also no need to pace the heart.

The roughening of the rounded tip edge or surface increases friction to prevent the tip from skidding over the heart surface, so that the tip can be reliably rolled over the beating surface of the heart by turning the barrel. The tip in one embodiment includes a tool which can act as a forceps or needle holder or driver. The very end of the tubular armature is bent over to form an anvil jaw, and a central rod running through the armature ends in, or is coupled to, a hammer jaw. The hammer jaw is movable by the surgeon via an actuating rod running through the armature. In this embodiment, a suturing needle grasped between the anvil jaw and hammer jaw can be manipulated by rolling the tip over the surface of the heart, and/or changing the angle of the armature by moving the barrel, to perform, for example, an anastomosis. The present invention contemplates the use of tips having various shapes and configurations for manipulating an implement such as a needle while rolling the tip: for example, a shape like a French curve or a lobed shape.

The industrial applicability is in cardiac surgery. A problem solved by the invention is following heart motion without adjustment.

BRIEF DESCRIPTION OF THE DRAWING

The above and other objects and the nature and advantages of the present invention will become more apparent from the following detailed description of embodiments taken in conjunction with drawings, wherein.

DETAILED DESCRIPTION OF THE PREFERRED EMBODIMENT

Here, and in the following claims:

"Armature" means any rigid or self-supporting member which may support or include at a tip end any sort of surgical instrument, device, or tool (e.g, stapler or clamping jaws), surgical material (e.g. suture thread), or diagnostic tool which can be supported by a handle to have at least one degree of freedom relative to the handle.

"Degree of freedom" has the usual meaning from physics and covers both translations and rotations. A completely free body has six degrees of freedom because it can move about in space in three directions and can also spin about three axes. A body such as the armature of FIG. 1, which can slide in the axial direction and rotate in the guide bearing in two directions (about two axes orthogonal to the barrel axis), has three degrees of freedom; if it could rotate about the barrel axis as well as move along the barrel axis, it would have four. Here, and in the following claims, "degree of freedom" may mean a degree of freedom over at least a small region. The tip motion, which actually includes two arcs, is approximated by three translations.

"Moving organ" includes any organ of the human body or an animal body which is capable of motion relative to the rest of the body, for example by muscle contraction, peristalsis, or twitching.

"Spring" includes any element having a relationship between force and distance.

"Tool" or "surgical tool" means any device for medical diagnosis or measurement, tissue manipulation, cutting or joining, or other treatment associated with any medical or surgical procedure.

"Unitary" means without any means for being dissembled, i.e., not knock-down and not to be taken apart without damage.

"Integral" means formed of or including at least one single piece of material.

Figure 1:
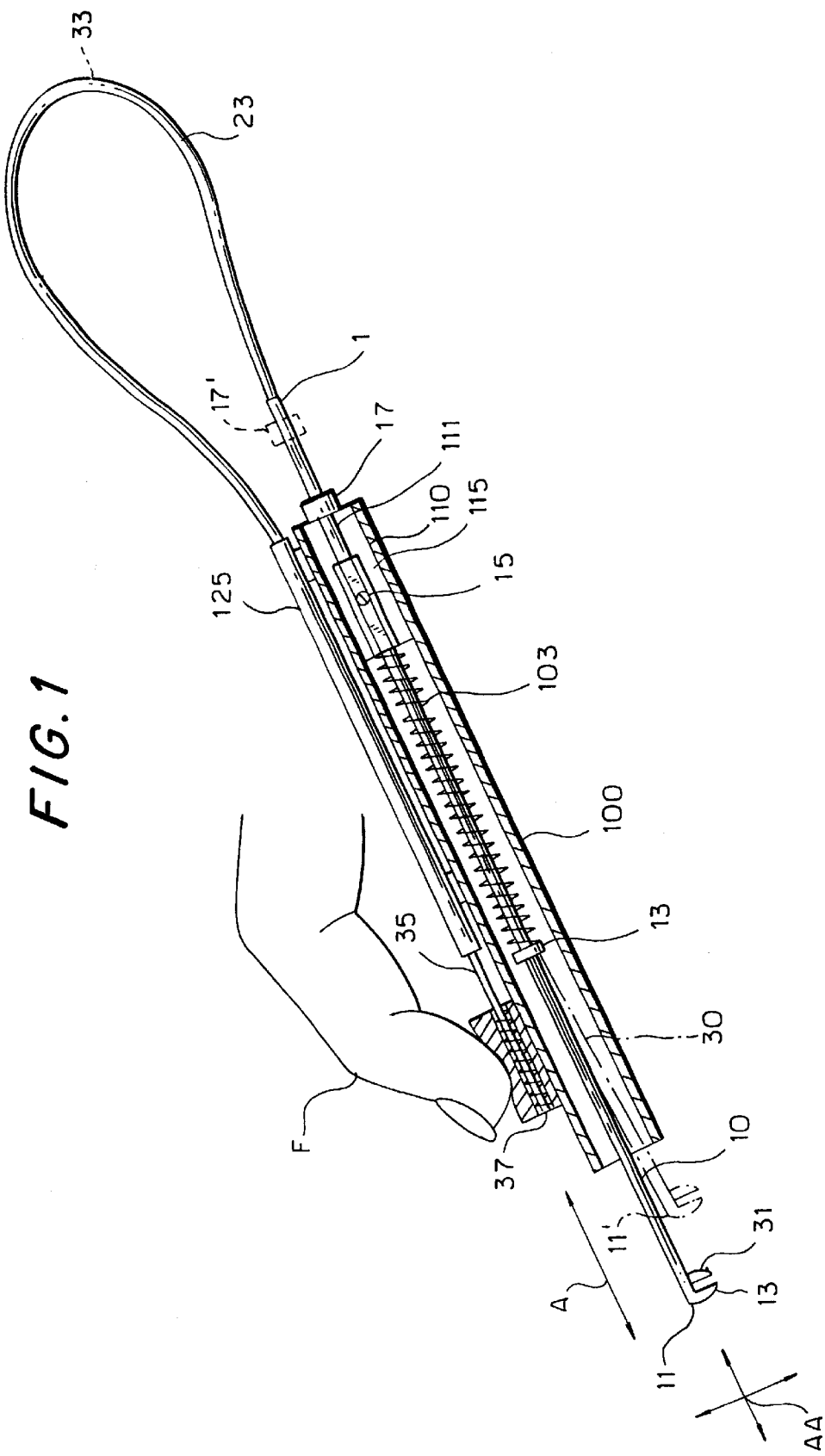
FIG. 1 is a cutaway view of a first embodiment of the invention.
Figure 2:
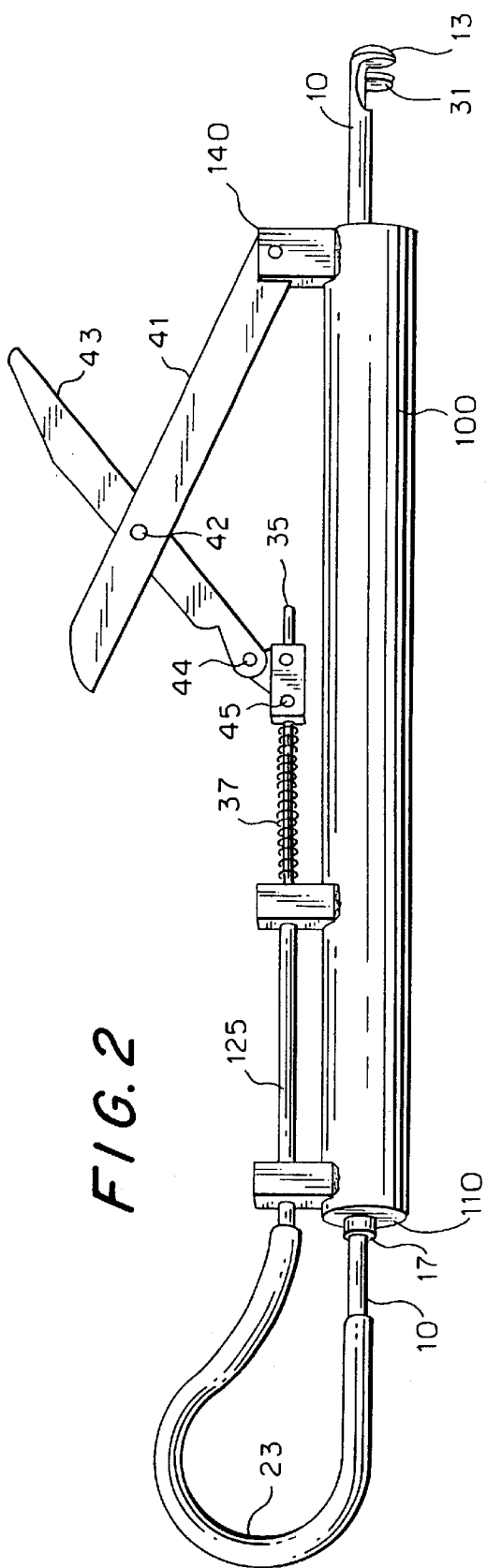
FIG. 2 is perspective view of an embodiment similar to that of claim 1 but with a different actuator.

FIG. 1 shows the invention in cutaway or cross-sectional view, while the outside of a similar embodiment is shown in FIG. 2. In FIG. 1 (but not in FIG. 2) the full length of the armature 10 is visible, from the tip 11 to the coupling or joint 12 joining the armature 10 to the hollow flexible cable guide 20. The armature 10 is preferably a straight length of stainless steel tubing, which is light but stiff and can be sterilized. A large portion of the length of the armature 10 is inside the barrel 100, which is also preferably of round stainless tubing.

The armature 10 interacts with the barrel 100 at the guide bearing 110 fixed inside the rear end of the barrel 100 (or at any other location along the axis of the barrel, or elsewhere). The guide bearing 110 is preferably made of slippery engineering plastic such as DELRIN or TEFLON. It has a central guide hole 111 which may be chamfered at either end so as not to restrict the angular orientation of the armature 10 in the guide bearing 110. The crossed arrows AA adjacent the tip 11 indicate the two planes or direction vectors in which the tip 11 may swing.

A coil spring 103 surrounds a portion of the armature 10 inside the barrel 100. This tracking spring 103 maintains a forward bias on the armature 10, being contained between a forward armature collar 13 and the guide bearing 110 so that it resists backward motion of the armature 10. In conjunction with the anti-skidding rough surface of the tip 11, it takes up slack in the direction of the arrow A and keeps the tip against the heart surface.

To maintain pretension in the tracking spring 103 a rear armature collar 17 is positioned on the armature so that the tracking spring 103 cannot fully extend. The position of collar 17 on the armature 10, like that of the other collars, is preferably adjustable for varying the pretension.

A displaced phantom armature 10 is shown in dot-dash lines, where the tip is indicated by 11' and the rear armature column by 17'; the axial direction of motion, which corresponds to the displacement of the phantom armature, is indicated by the arrow A. All three arrows A and AA are preferably mutually perpendicular.

The tracking spring 103 may be as long as geometrically feasible to maintain a nearly constant force of the tip 11 on the heart regardless of the distance of the barrel 100 from the heart, or, it may be made shorter for a variable force.

At the tip 11 FIGS. 1 and 2 show an anvil jaw 13 of the armature 10 and a mating hammer jaw 31 which is an extension of a rod 30 slidable inside the armature 10. The jaws 13 and 31 are preferably brazed onto the armature 10 and rod 30, have diamond-studded jaw gripping surfaces, and roughened sides for anti-skidding friction against a body organ. The jaws 13, 31 may be used as a forceps, or to grip a suture needle.

The rod 30 pushes the hammer jaw 31 to grip under actuation of the surgeon's finger F, as follows: The rear end of the rod 30 is connected internally (not shown) to a flexible cable or chain-like element 33 (not visible) which slides within the hollow flexible cable guide 23, which in turn is connected (not shown) to a second rod 35 attached to a fingerpad 37 for sliding actuation. The second rod 35 slides within a guide tube 125 fastened to the barrel 100 as the first rod 30 slides inside the armature 10 (but in the opposite direction). Any linkage, not only a flexible cable, can be used in the present invention.

To prevent rotation of the armature and the jaws 13, 31 about the longitudinal axis of the barrel 100, the armature 10 includes a lateral pin 15 engaged in a slot 115 of the guide bearing 110.

FIG. 2 shows a preferred alternative to the sliding finger-pad 37 of FIG. 1, in which the jaw actuator has a different manipulating portion. Surrounding the second rod 35 between the guide tube 125 and a second rod collar 45 is a jaw-opening spring 47 which tends to open the jaws 13, 31 by retracting the hammer jaw 31 (to the left in FIG. 2). To counteract the force of the jaw-opening spring 47 and grip a needle, operate a stapler, etc., the surgeon presses the levers 41 and 43 toward the barrel 100. Being hinged at pivot points 140 on the barrel 100, 44 on the second rod collar 45, and to each other at pivot 42, the levers as they collapse push the second rod collar 45 and the second rod 35 to the left, causing the jaws 13, 31 to close. Because of the leverage the gripping force is increased over the embodiment of FIG. 1.

Figure 3:
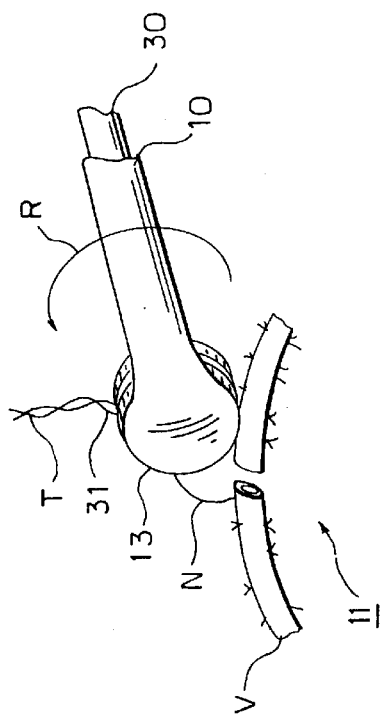
FIG. 3 is an enlarged perspective view of the armature tip of FIGS. 1 and 2.

FIG. 3 shows an example of the present invention in use at an anastomosis site with blood vessel V. The surgeon grips a curved suture needle N with attached suture thread T between the jaws 13, 31 by sliding the finger pad 37 rearward (in FIG. 1, to the right). While holding this grip with the finger F of FIG. 1, the surgeon rolls the tip 11 by rotating the barrel 100 so that the outer surface of the anvil jaw 13 (and/or the outer surface of the hammer jaw 31) roll over the organ surface to pierce the blood vessel V on the organ surface (e.g., the beating heart) with the tip of the needle N, so as to perform an anastomosis. The tip 11 is placed into the proper position, where it stays by friction, and then the barrel 100 is rotated about its axis to pierce the wall of the blood vessel V. The tip of the needle N will describe an approximate cycloid curve when the rolling edge of the tip 11 is circular in profile.

Figure 4:
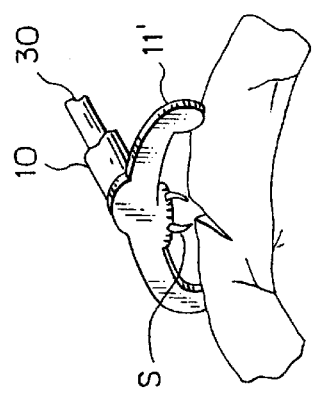
FIG. 4 is an enlarged perspective view of a stapler embodiment of the armature tip.

FIG. 4 shows an alternative embodiment with a tip 11' having a stapling mechanism; a staple S is shown. The tip 11' includes a lobed outline adapted to "walk" over the organ surface. In this embodiment the rod 30 may actuate the stapling mechanism, parts of which move relative to the tip 11 (e.g., the stapling anvil shown above the staple in FIG. 4). Alternatively, the mechanism may be actuated by fluid pressure and the armature 10 be adapted to hold a supply of staples S (not shown).

Rather than being completely free to rotate about the guide bearing 110, the armature 10 may include resilient or other centering devices (not shown) which tend to center the armature 10 in the barrel 100; for example, a block of resilient material or elastomer surrounding the armature near the guide bearing 110 with a central ring of TEFLON or the like through which the armature 10 slides, or, an elongated extension of the guide bearing 110 without excessive chamfering of the ends of the guide hole 111. The centering may be such that the light-weight armature will not fall against the rim of the barrel of its own weight.

Figure 5:
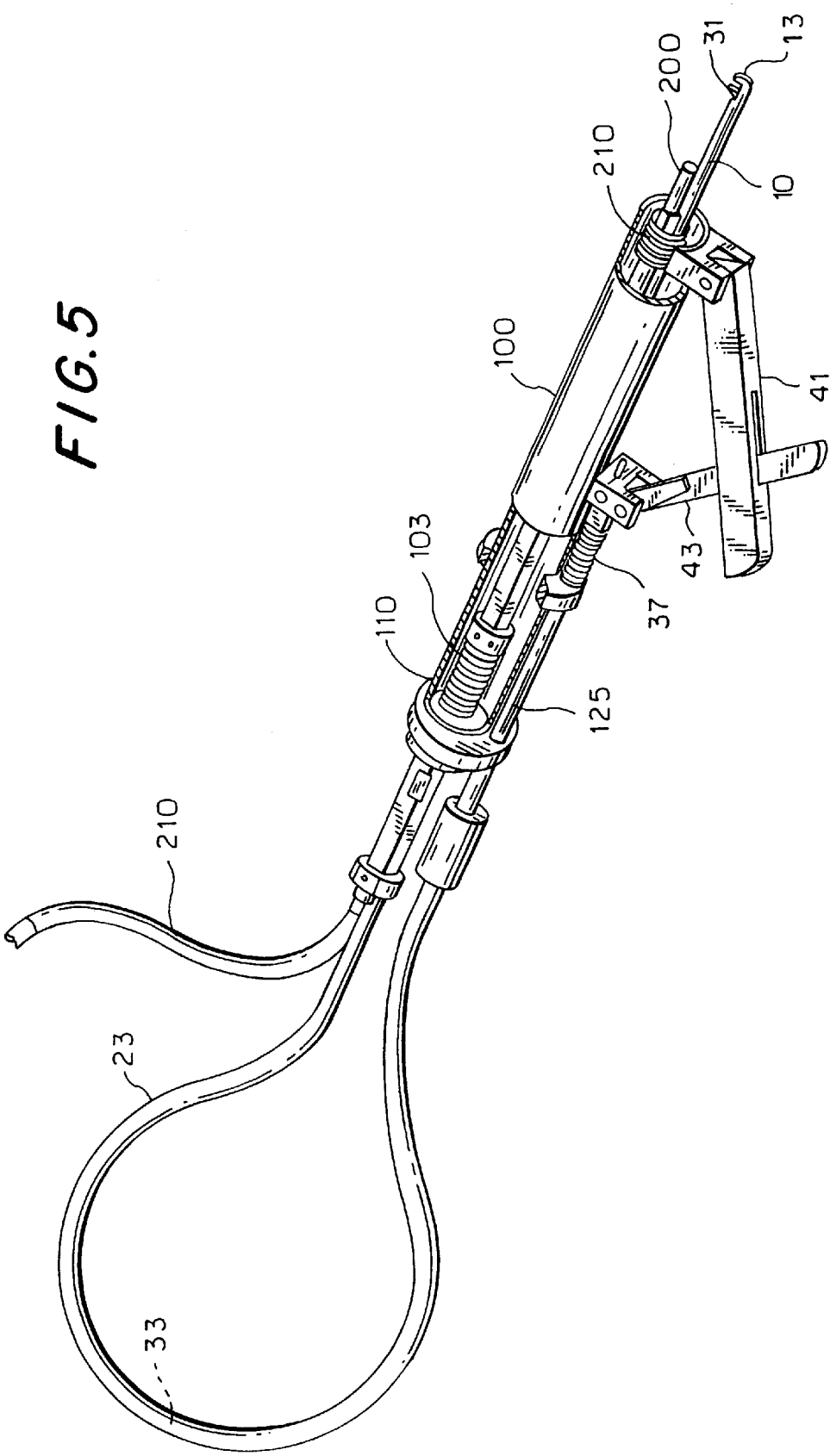
FIG. 5 is a perspective, partially cut-away view of an embodiment with a video camera attached.

FIG. 5 shows an embodiment of the present invention with a miniature video camera 200, mounted on the armature 10 to reciprocate along with it and optionally removable. The camera 200 is focused on the region of the jaws 13, 31, and the image is conveyed from the camera 200 via a link 210 to an external imaging device such as a CRT. The link 210 may be, for example, electronic, a fiber optic, or a fiber-optic bundle. This arrangement allows the surgeon to view the jaws 13, 31 and their work as if they were stationary, since the reciprocation of the camera 200 virtually "stops" the heart.

Optionally, a centering spring 210 is mounted in the end of the barrel 100 to provide an additional centering force. In FIG. 5 the barrel 100 is depicted as partially cut away to show the internal parts.

In alternative embodiments not shown in the drawing, the present invention may include an armature which is not rotatably locked to the barrel or other handle, and thus has four degrees of freedom relative to the handle rather than the three degrees of freedom of the illustrated embodiment. (It may also have six, five, two, or one degree of freedom relative to the handle). If, for example, the armature tip includes legs that are movable relative to the armature for "walking" over the organ surface, wheels for rolling over the surface, a miniature sewing machine which automatically advances along the surface while it sews, any other self-moving tip arrangement, this is within the scope of the invention. The present invention comprises any means for moving the tip over the surface whatsoever, whether by manipulation of the handle (such as for example the rolling of FIG. 3), by moving the handle about (e.g., the embodiment of FIG. 4), or by some other control, e.g. computer/servo control or surgeon-operated pneumatic, hydraulic, or electric control or power.

In addition to friction, the present invention includes any means for holding to or gripping the surface of an organ and any means for preventing sliding over the surface of any organ. Such means may include a plurality of small sharp points, pincers, adhesive, suction, screw-threads, and so on. The present invention includes a tip fastened to a site on the heart by adhesive or the like so as to move along with the site, where the tool mounted on the tip includes a robotic or remote-control mechanism operating next to the tip or through a hole in the tip within an incision into or through one or more layers of the heart (or other organ). A tip having a relatively large "footprint" would provide a stable base for operating on adjacent or interior portions of the heart by a tool movable relative to the tip. With suitable miniaturized motion-canceling mechanisms like those of the inventor's earlier inventions discussed above, the relative motion between the tip and an interior structure of the heart could be canceled.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A surgical instrument for operating on a site on a moving body organ while automatically following the motion of the site; the instrument comprising:

a handle;

an armature having a tip composed of substantially rigid elements, the armature being coupled to the handle by a coupling giving to the tip at least three degrees of freedom relative to the handle in response to the motion of the site, whereby the tip is unconstrained;

the armature tip comprising a surgical tool;

whereby the unconstrained tip and the surgical tool may remain on the moving organ site during use while the handle does not move.

2. The surgical instrument according to claim 1, wherein the tip comprises an anti-skid surface.

3. The surgical instrument according to claim 1, wherein the anti-skid surface is rough.

4. The surgical instrument according to claim 1, comprising a remote tool actuator.

5. The surgical instrument according to claim 1, comprising a tool actuator mounted on the handle.

6. The surgical instrument according to claim 5, comprising a flexible actuating coupling between the surgical tool actuator and the surgical tool.

7. The surgical instrument according to claim 5, wherein the surgical tool actuator includes a lever arm (41) coupled to the handle such that squeezing of the lever toward the handle actuates the surgical tool.

8. The surgical instrument according to claim 1, wherein the surgical tool comprises gripping jaws.

9. The surgical instrument according to claim 1, wherein the surgical tool comprises a stapler.

10. The surgical instrument according to claim 1, comprising a spring urging the armature in a direction toward the site.

11. The surgical instrument according to claim 10, wherein the armature is elongated in direction toward the site.

12. The surgical instrument according to claim 11, wherein the handle comprises a tubular hollow barrel open at a forward barrel end closest to the tip and the direction is generally parallel to an axis of the barrel.

13. The surgical instrument according to claim 12, wherein the armature is elongated and the handle comprises a guide bearing wherein the armature is slidably movable.

14. The surgical instrument according to claim 13, wherein the armature is held against rotation about a rotation axis substantially parallel to the axis of the barrel.

15. The surgical instrument according to claim 1, wherein the handle is elongated and has an axis, and wherein the armature is slidable relative to the handle in a direction generally parallel to the axis and is pivotable relative to the handle in directions generally perpendicular to the axis, whereby the three degrees of freedom include one sliding motion and two rotational motions.

16. The surgical instrument according to claim 15, wherein a spring urges the armature in a direction corresponding to at least one of the degrees of freedom.

17. The surgical instrument according to claim 1, wherein a portion of the tool is movable relative to the tip.

18. The surgical instrument according to claim 17, wherein the portion of the tool movable relative to the tip includes at least one gripping jaw.

19. The surgical instrument according to claim 17, wherein the portion of the tool movable relative to the tip drives surgical staples.

20. The surgical instrument according to claim 1, comprising a video camera mountable on the armature and focusable on the tip of the armature.

* * * * *